United States Patent [19]
Van Hengel et al.

[11] Patent Number: 5,317,387
[45] Date of Patent: May 31, 1994

[54] METHOD OF AND APPARATUS FOR NON-DESTRUCTIVE COMPOSITE LAMINATE CHARACTERIZATION

[76] Inventors: Cornelis G. Van Hengel, Roland Holstlaan 1078, 2624 JR Delft; Hendrik A. Vuil, Bickerlaan 10, 2071 DC Santpoort, both of Netherlands

[21] Appl. No.: 807,939

[22] Filed: Dec. 16, 1991

Related U.S. Application

[63] Continuation of PCT/NL90/00045, Apr. 12, 1990.

[30] Foreign Application Priority Data

Apr. 14, 1989 [GB] United Kingdom ............... 8908507

[51] Int. Cl.$^5$ .................................................. G01B 11/00
[52] U.S. Cl. ....................................... 356/372; 356/446
[58] Field of Search ................ 356/364, 369, 370, 372, 356/241, 445, 446

[56] References Cited

U.S. PATENT DOCUMENTS

| | | | |
|---|---|---|---|
| 3,417,745 | 12/1968 | Sheldon | 128/6 |
| 3,761,186 | 9/1973 | Wason | 356/241 |
| 3,971,918 | 7/1976 | Saito | 235/92 |
| 4,030,827 | 6/1977 | Delhaye et al. | 356/301 |
| 4,041,286 | 8/1977 | Sanford | 235/151.3 |
| 4,277,168 | 7/1981 | Oku | 356/138 |
| 4,281,929 | 8/1981 | Lord et al. | 356/241 |
| 4,440,496 | 4/1984 | Milana | 356/241 |
| 4,557,598 | 12/1985 | Ono et al. | 356/241 |
| 4,606,645 | 8/1986 | Matthews et al. | 356/446 |
| 4,657,387 | 4/1987 | Heising et al. | 356/72 |
| 4,930,889 | 6/1990 | Van Donselaar et al. | 356/237 |

FOREIGN PATENT DOCUMENTS

| | | |
|---|---|---|
| 0086546 | 8/1983 | European Pat. Off. . |
| 1445685 | 8/1976 | United Kingdom . |
| 1525856 | 9/1978 | United Kingdom . |
| 1597005 | 9/1981 | United Kingdom . |
| 2184233 | 6/1987 | United Kingdom . |

OTHER PUBLICATIONS

IBM Technical Disclosure Bulletin, vol. 25, No. 10, (Mar. 1983) "Drill Hole Optical Inspection Tool".
SPIE vol. 566 (1985) "Fiber Optic and Laser Sensors III" pp. 159-163.
Materials Evaluation, vol. 39, No. 10, pp. 922-925, (Jun. 1980) "Nondestructive Composite Laminate Characterization by Means of Ultrasonic Polar-Scan".

Primary Examiner—F. L. Evans
Attorney, Agent, or Firm—Bachman & LaPointe

[57] ABSTRACT

A method for the non-destructive determination of the stacking order and the fiber orientation of a fiber reinforced composite laminate comprises illuminating optically successively a series of spots of a cross sectional surface of the laminate under examination and detecting light radiated from the respective illuminated spots. An electrical output signal relative to the amount of light detected is provided and a characterization of the laminate indicative of the stacking order and fiber orientation is determined from the electrical output signal. An apparatus is provided for carrying out the method of the present invention.

15 Claims, 4 Drawing Sheets

METHOD OF AND APPARATUS FOR NON-DESTRUCTIVE COMPOSITE LAMINATE CHARACTERIZATION

This application is a continuation of International Application PCT/NL90/00045 filed on Apr. 12, 1990 and which designated the United States.

FIELD OF THE INVENTION

The present invention relates to a method and an apparatus for non-destructive composite laminate characterization, in particular for the determination of the stacking order and the fiber orientation of a fiber reinforced laminate.

BACKGROUND OF THE INVENTION

Composite laminates, such as CFRP (Carbon Fiber Reinforced Plastic) material, i.e. a laminated structure composed of several layers of carbon fiber tape embedded in a synthetic resin, are of great interest for the aviation industry because of the high strength to weight ratio. For primary structures this high ratio is mainly achieved by optimizing the ply orientation and stacking sequence in a CFRP laminate, with respect to the direction of tensile and compressive strains acting upon the structure. A difference between the designed and produced stacking sequence can result in a drastic reduction of the mechanical strength of said structure. Other advanced composite laminates are for example aramide fiber and E glass fiber reinforced structures. Laminates of light weight metal plates, adhered together by means of a fiber embedded resin, are also of special interest for the aviation industry.

To check whether a laminated product meets the quality requirements forthcoming from airworthiness and safety regulations for aero space vehicles, several inspections have to be carried out. For example, during the last phase of manufacture there must be verified whether the prescribed manufacturing process has yielded a composite laminate in which the fiber/resin composition in all important areas meets the initial design phase. Further, upon repair it is also often necessary to determine the laminate composition in terms of stacking order and fiber orientation.

A non-destructive method for verifying the correct position of the load carrying fibers in a composite, is an ultrasonic method which is based on ultrasound refraction. The method is described in "Non-destructive Composite Laminate Characterization by Means of Ultrasonic Polar Scan", by W. H. M. van Dreumel and J. L. Speijer, in Materials Evaluation, vol. 39, no. 10 (1981), pp. 922-925. For the "Polar-Scan" method the laminate or product to be inspected is attached to a turn table and two ultrasonic tranducers are positioned at a certain angle at both sides of the laminate, one being used as a transmitter and the other as a receiver. The entire combination is placed in a tank which is filled with a liquid that permits transmission of longitudinal waves from the transmitter to the receiver. A transmitted signal is detected as an interference product of several wave modes and their reflections. This interference pattern strongly depends on the laminate configuration.

However, the "Polar Scan" method offers no direct quantitative data, in terms of stacking order and fiber orientation of a fiber reinforced laminate, but only a reasonable qualitative impression is obtained of the directional elastic properties of the laminate as a hole. A further drawback can be that the product under inspection has to be submerged in a tank. The method promises no small scale test instrument, for example to be used directly in the production line for carrying out an end-product inspection.

Yet another ultrasonic test method is given by EP-C-0,086,546. The advantage of the method described over the "Polar-Scan" method is that discrete data about the laminate stacking order and the layer orientation are produced. The described "CompoScan" device requires in principle no moving parts and the probe is simply placed on the surface of the laminate to be inspected. A contact fluid is necessary. However, the method does not offer reliable data in the case of laminates having a plurality of layers.

A more direct method of measuring the position of load carrying fibers in the composite laminate, used in practice, is the visual inspection by microscope of a transverse section of the laminate. However, the method gives information about the edges of the product only. When the number of weaves, their sequence and the orientation of the fiber varies from one location to another, due to the loading configuration of the structure, a full inspection of the end-product by microscope in a non-destructive manner is not possible. The only solution then is to take a sample of the laminate to be inspected, and making several angularly displaced transverse sections having different angles with respect to an edge or an imaginary edge of said sample. However, in practice such a destructive inspection is neither possible in most practical cases. Further, this direct method is not suitable for a quick inspection in, for example, a production line environment.

Another destructive, very time consuming and complex method for the inspection of composite laminates is the so-called pelling method, also used in practice. In this pelling method, the laminate to be inspected is heated above a temperature at which the synthetic resin, in case of a CFRP laminate the carbon fibers are embedded in, burns to leave the several layers of carbon fibers. By pelling these layers, the stacking order and fiber orientation can be easily determined. Although the results obtained with this method are very reliable, due to its complexity and its time consuming and destructive character, this pelling method is neither suitable for a quick inspection in, for example, a production line environment.

OBJECTS OF THE INVENTION

It is, therefore, the principal object of the present invention to provide a method for non-destructive composite laminate characterization with which quantitative data of the stacking order and the fiber orientation of a fiber reinforced laminate can be obtained, in a relatively fast and easy to perform manner.

Another object of this invention is to provide the characterization of the composite laminate suitable for a quick examination of the results obtained.

Yet another object of the invention is to provide an apparatus for carrying out this method, said apparatus being easy to handle and suitable for use in a production line environment.

Still another object of the present invention is to provide an apparatus which allows for a "go" or "no-go" result of the composite laminate under examination.

SUMMARY OF THE INVENTION

These objects and others which will become apparent hereinafter are obtained, in accordance with the present invention, by illuminating optically successively a series of spots of a cross-sectional surface of a laminate under examination; detecting light radiated from respective illuminated spots; providing an electrical output signal relative to the amount of light received; and forming from said electrical output signal a characterization of the laminate under examination indicative of the stacking order and the fiber orientation thereof.

By making in a fiber reinforced composite laminate a small hole perpendicular to the outer surface of the end-product i.e. perpendicular to the layers of the composite laminate, such as a CFRP-laminate, the surface of said hole shall show in longitudinal and tangential direction at least a regular pattern of variations of cut-through or grazed fibers, embedded in a synthetic resin. The variations in said pattern depend on the stacking order and the fiber orientation of the composite laminate. At a certain depth in the hole, while rotating 360 degrees around the longitudinal axis thereof, an intersection of a particular layer of fibers can be observed. It is found that by illuminating optically different spots of the inner surface of the hole, belonging to said layer, the amount of light radiated from said illuminated spots differs whether a spot belonging to a cut-through or a grazed fiber is illuminated. The amount of light received from an illuminated spot corresponding to a cut-through fiber is less than the amount of light received from a spot belonging to a grazed fiber.

By successively illuminating spots of the inner surface of said hole and by detecting the amount of light radiated from respective illuminated spots, the results obtained are indicative for the orientation of the weave or the unidirectional tape in the laminate. The measurement is repeated over the entire inner surface of the hole, in order to collect also information about the stacking order of the weave or tape. By providing an electrical output signal relative to the amount of light received and after processing of the signal thus obtained, the combined end-result contains quantitative information about the actual orientation of the layers and the stack sequence of the layers for the inspected area of the laminate.

The method is not limited to cross-sections being the inner surface of hole, but is also applicable to the outside surface of several transverse sections of a laminate having different angles with respect to an edge or an imaginary edge of said laminate, the outer surface of a core sample taken from the laminate by a hollow drill etc..

For carrying out the method according to the invention, use can be made of attaching holes or mounting holes in a given end-product, or a small hole can be drilled. By a proper choice of the area of the composite laminate where a hole is drilled or a core sample is taken, in general, no adverse effect on the mechanical strength properties of an end-product is caused. In the case of CFRP materials, it is observed that a cross-section having a non-finished surface provides very reliable data.

In most cases a homogeneous laminate has to be inspected. In such cases, the step of illuminating according to the invention, consists in illuminating successively a series of spots of a first and second sub-surface of said cross-sectional surface of the laminate under examination, said sub-surfaces being mutually reflection symmetric with respect to said illuminated spots, and wherein the step of forming a characterization of the composite laminate under examination includes forming from said first and second sub-surfaces a first and second characterization of said composite laminate respectively, and matching same for generating an indication of the reliability of the results obtained. In a homogeneous laminate both said sub-surfaces are expected to yield the same data. By matching same, an indication of the reliability of the result obtained can be generated.

From analysis point of view, a circle cylindrical hole or a circle cylindrical core sample are preferred. Said first and second sub-surface being one and another half of the inner surface of said hole or the outside surface of said core facing an imaginary plane of section in longitudinal direction of said hole or core including the center axis thereof.

By using data processing techniques, the obtained results can be presented in a number of ways. In another embodiment of the method according to the invention, the characterization of the composite laminate under examination is generated graphically as a patch pattern, each patch of which corresponds to a number of adjacently spaced illuminated spots, from which the amount of light received is within a given range. Such a patch pattern provides an easy to read representation of the composite laminate under examination.

In principle, said patches may have an arbitrary shape. However, in yet a further embodiment of the method according to the invention, the patches are generated such, that their dimensions correspond to the number of adjacently spaced illuminated spots, from which the amount of light received is within a given range. Patches of this type, for example, provide specific information about the thickness of layers in a laminate in case of layers of various thicknesses. By displaying the patches in different colours, corresponding to the amount of light received within a given range, a valuable easy to inspect characterization of said laminate can be obtained.

In a production line environment for example, where there is a need for a non-complicated measurement for making decisions of the type of "go" or "no-go" regarding the composite laminate under examination, yet another embodiment of the method according to the invention consists in forming an electrical representation of said composite laminate, and comparing same with a given similar known representation of said composite laminate. The result of said comparison is the required "go" or "no-go" information, which can be presented as a separate diagnostic message.

The apparatus for carrying out the method according to the invention comprises light source means, for illuminating optically a series of spots of a cross-sectional surface of a composite laminate under examination; detector means for generating an electrical output signal relative to the amount of light received from an illuminated spot; probe means, optically coupled with said light source means and detector means, for providing a light beam to be directed to said cross-sectional surface; drive means, for moving relative to each other said probe means and said cross-sectional surface of the composite laminate under examination; support means, supporting said light source means, detector means, probe means and drive means, said support means having adjustment means for adjusting said cross-sectional surface of the composite laminate under examination and said probe means; and processor means, equipped for controlling said drive means in a programmable manner, and for processing the electrical output signal of said detector means to generate a characterization of the composite laminate under examination indicative of the stacking order and the fiber orientation thereof.

The measurement can be improved by providing polarizer means for illuminating the series of spots of the surface of the cross-section of the composite laminate under examination with light of a first polarization, and means for directing to the detector means light of a second polarization, received from an illuminated spot. By using polarized light, the influence of scattering or diffraction on the measurement can be limited to a larger extent.

To provide as much as freedom in the manner of scanning the surface of the cross-section of the composite laminate under examination, the processor means in the apparatus according to the invention may have storage means, for storing the electrical output signal of the detector means in relation to the controlling of the drive means. Data stored can be processed and displayed on display means in the form desired, for instance graphically as a patch pattern, in numerical form as a table, in words or other suitable representation.

Methods and apparatus for optically scanning a surface are known per se from U.S. Pat. Nos. 3,761,186 and 4,440,496. However, the apparatuses described in these U.S. Patents are designed for optically inspecting the condition of a surface of a hollow cylindrical workpiece, for example which has undergone mechanical treatment such as finishing by grinding or the like, or to inspect surfaces for purposes of detecting the existence of flaws thereon. Neither of these patents suggest or describe an optical scanning method or apparatus as described above for the characterization of fiber reinforced composite laminates, in terms of stacking order and fiber orientation.

BRIEF DESCRIPTION OF THE DRAWING

The above and other objects, features and advantages of the present invention will become more readily apparent from the following description, reference being made to the accompanying drawing in which.

DETAILED DESCRIPTION OF THE INVENTION

Figure 1:
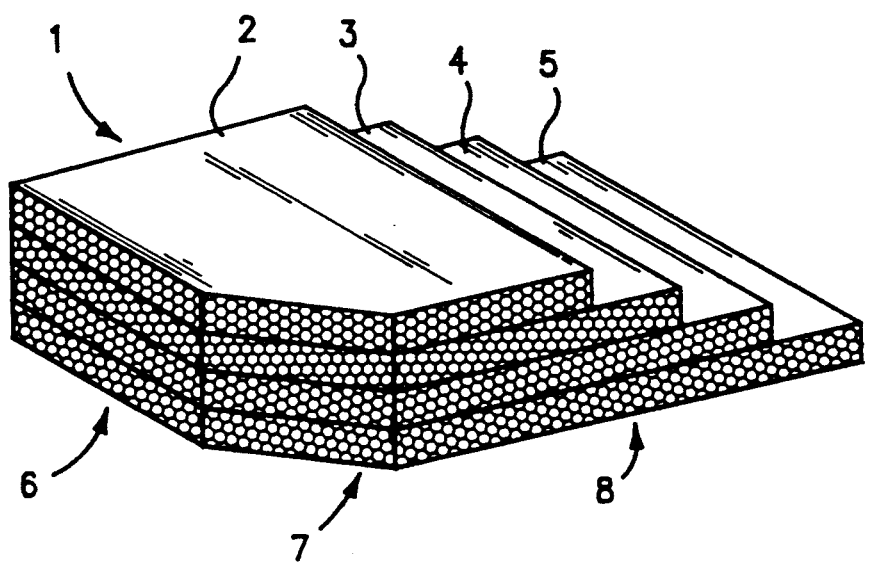
FIG. 1 is a diagrammatic perspective view of a four layer, fiber reinforced composite laminate, on a greatly enlarged scale with respect to laminates used in practice, showing different edge sections.

FIG. 1 shows in perspective a diagrammatic view of a so-called angle-ply composite laminate, for example a CFRP (Carbon Fiber Reinforced Plastic) material. The angle between the fibers in the top layer 2 and the bottom layer 5 as well as the angle between the fibers of the inner layers 3 and 4 is 90°. The angle between the layers 2 and 3 and the layers 4 and 5 is 45°. The orientation of the fibers of the respective layers can be seen at the sections 6, 7 and 8 at the edges of said composite laminate 1. For illustrative purposes, the direction of the fibers in a layer is also indicated by hatching of the surfaces thereof.

In practice, the thickness of the layers 2-5 varies from 0.1-0.2 mm the respective fibers having a diameter about 0.01 mm. Laminates having a number of layers up to 300 are no exception. Of course, other ply-angle composites are possible, dependent on the direction of the tensile forces in the end-product.

Figure 2:
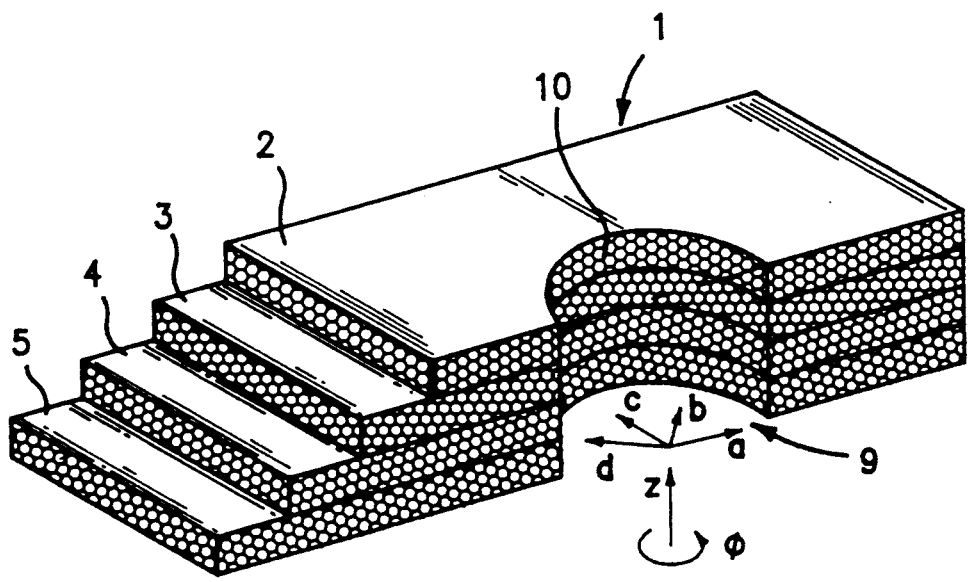
FIG. 2 is a view similar to FIG. 1, having a through bore hole.

FIG. 2 shows a sectional view of the composite laminate of FIG. 1, having a through hole 9, the inner surface 10 of which shows either cut-through or grazed fibers, dependent on the orientation thereof.

Figure 3:
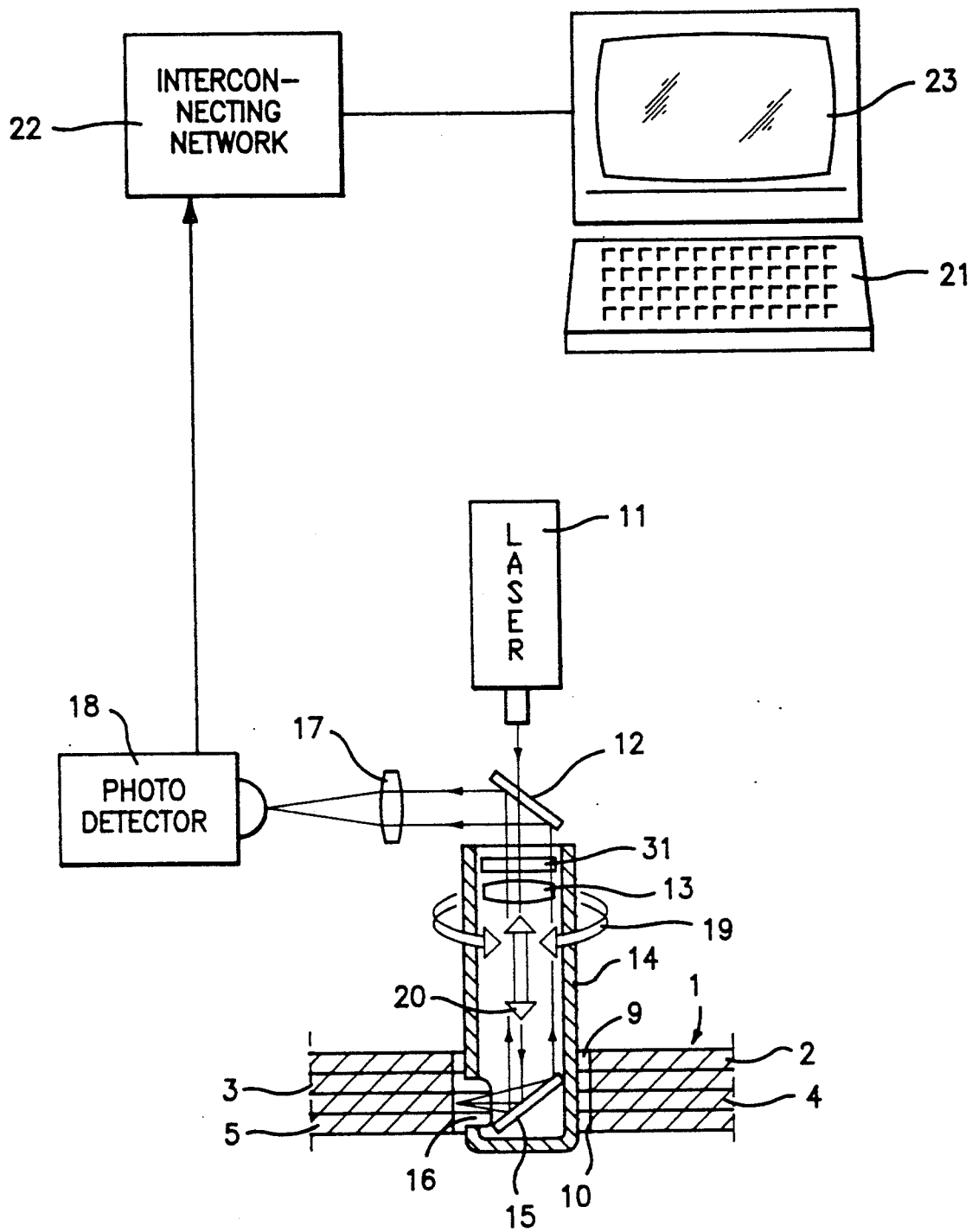
FIG. 3 is a diagrammatic illustration of an apparatus for carrying out the method according to the invention.

FIG. 3 shows diagrammatically the main elements of the apparatus according to the invention. A light source 11 of laser energy is provided, the output beam of which is directed through a semi-transparent diagonal mirror 12 and a focusing lens 13 at an open end of a probe 14 to a reflecting diagonal mirror 15 arranged at the end of said probe facing the focusing lens 13. Instead of a semi-transparent mirror 12, a mirror 12 having a hole for passing through the light beam of the source 11 may be used. The probe 14 consists of a tube of non-transparent material, having at the end near the reflecting diagonal mirror 15 an aperture 16 for the illumination of the inner surface 10 of the hole 9 in the composite laminate 1 of FIG. 2, for example. The outer diameter of the probe 14 can be about 4 mm or even smaller.

The light received from a respective illuminated spot of the inner surface 10 is directed via the aperture 16 and the reflecting diagonal mirror 15, the probe 14, the focusing lens 13 and the reflecting surface diagonal mirror 12 to another focusing lens 17 and to a photoelectric detector 18, for example a photo-electric cell. For simplicity, the drive means for moving the probe 14 crosswise and lengthwise of the hole 9 in the laminate 1 under inspection are represented by double arrows 19, 20 respectively. Although the apparatus in FIG. 3 is illustrated as scanning the inner surface of a hole in the laminate, it is obvious for one skilled in the art that said probe means can also be used for inspecting the edge surfaces of a laminate or the outer surface of core sample. By using polarizer means 31 for illuminating the surface under inspection with light of a first polarization, and polarizer beam splitter means 12 for directing to the detector 18 light of a second polarization, received from an illuminated spot, the influence of detrimental scattering or diffraction effects on the measurement can be limited.

The optical configuration shown is substantially similar to that of U.S. Pat. Nos. 3,761,186 and 4,440,496. However, the apparatuses described in these U.S. Patents are designed for optically inspecting the condition of a surface of a hollow cilindrical workpiece, for example which has undergone mechanical treatment such as finishing by grinding or the like, or to inspect surfaces for purposes of detecting the existence of flaws thereon. Neither of these patents suggest or describe the use of said apparatuses for the characterization of composite laminates, for which the apparatus according to the invention comprises processor means 21, connected via an interconnecting network 22 to the photo-electric detector 18 and the drive means, for controling said drive means in a programmable manner and for processing the electrical output signal of the detector 18, such to generate a characterization of the composite laminate, indicative of the stacking order and the fiber orientation thereof.

The processor means 21 comprises a video monitor 23, preferably a colour video monitor, for displaying the obtained characterization of the composite laminate under inspection. For purposes of storing data obtained, the processor 21 is provided with adequate storage means.

Figure 4:
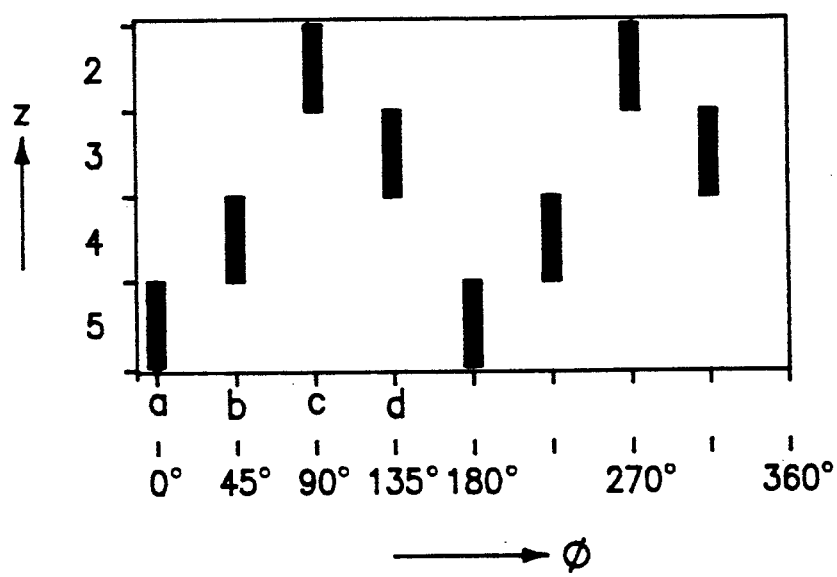
FIG. 4 is an illustration of a patch pattern obtained from the laminate according to FIG. 2.

FIG. 4 shows a patch pattern according to the present invention, obtained by inspection of the laminate 1 of FIG. 2. Along the abscissa the angle of rotation $\phi$ of the probe is indicated, starting at a in FIG. 1, i.e. $\phi=0°$, via b, c, d and so on up to $\phi=360°$. In ordinate direction z the respective layers 2, 3, 4, 5 can be distinguished. The patch pattern is such, that when the amount of light received from respective illuminated spots is at a maximum, a patch is indicated. In CFRP laminates, this is at spots corresponding to grazed fibers. According to FIG. 2, at an angle of $\phi=0°$ corresponding to a, the greatest amount of light is received from the illuminated spots corresponding to layer 5. At an angle of $\phi=45°$, corresponding to b, the spots of layer 4 will yielded the most amount of light, at $\phi=90°$ corresponding to c, the spots of layer 2 will produce same, and at $\phi=135°$, corresponding to d, the amount of light received from the illuminated spots of layer 3 will be at a maximum. Due to the symmetry of the composite laminate 1, the same result will be obtained from $\phi=180°$ to $\phi=360°$, providing there have been no defects in the laminate 1. The patch pattern presented in FIG. 4, is characteristic for the stacking order and fiber orientation of the composite laminate 1 shown in FIG. 2.

It is observed that the least amount of light is received from illuminated spots corresponding to the transverse cross surface of cut-through fibers. The amount of light received from fibers, which are cut-through via a plane diagonal compared to their longitudinal direction, will between said least amount and the maximum amount corresponding to grazed fibers. By using an appropriate processing algorithm, which may include default measurement settings the light received within given ranges can be converted into patches of certain dimensions, colours etcetera, for obtaining a sophisticated characterization of the laminate under inspection.

Figure 5:
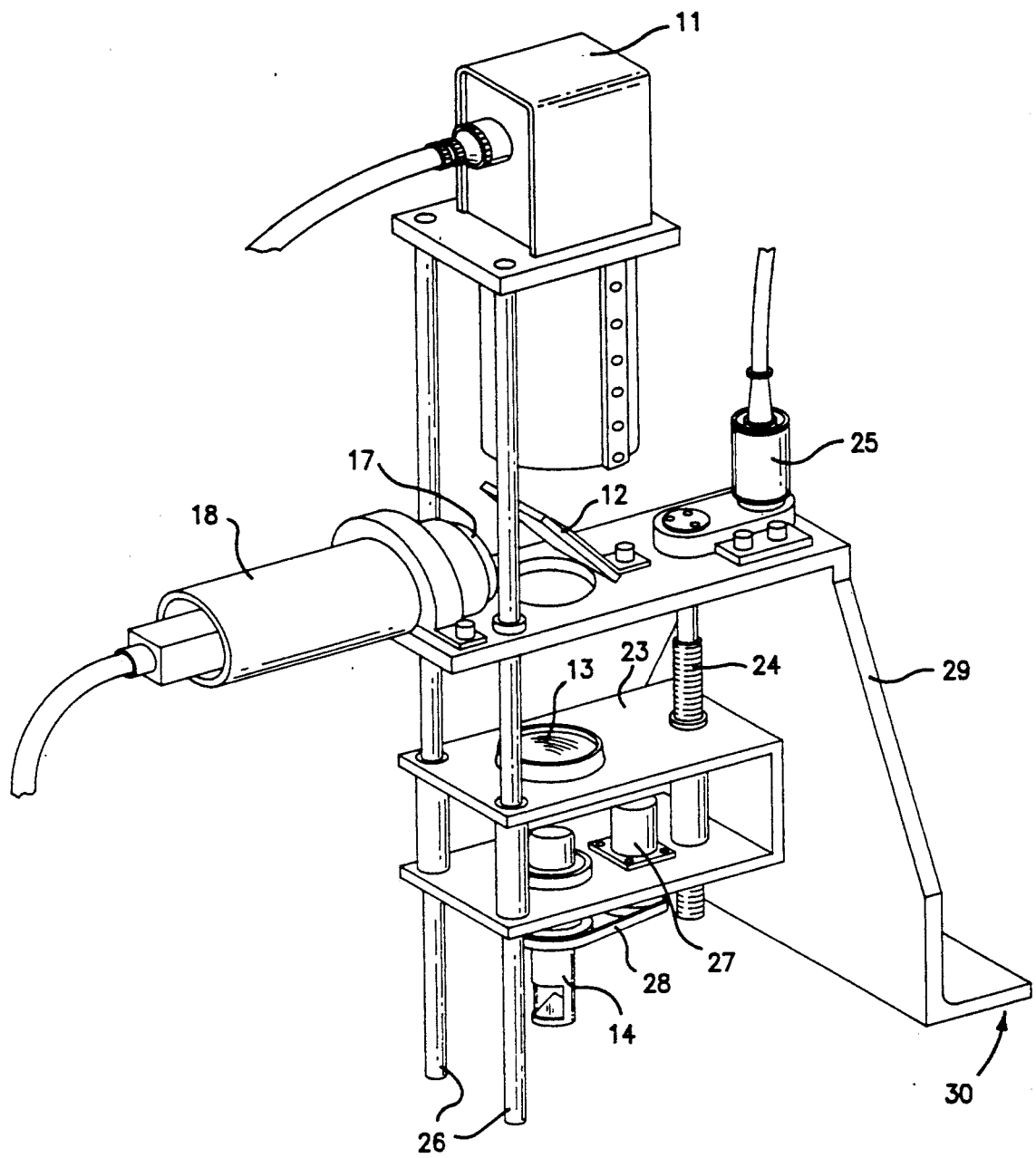
FIG. 5 is a perspective diagrammatic view of an embodiment of the apparatus according to the invention.

FIG. 5 shows a perspective diagrammatic view of an embodiment of the apparatus according to the invention. The elements corresponding to FIG. 3 are indicated with the same reference numerals. The probe 14 and the focussing lens 13 are mounted at a frame 23, which can be moved by means of a spindle 24 and a first servo-motor 25 along guides 26 in the longitudinal direction of, for example, a hole in a laminate to be tested. For moving the probe 14 in tangential direction of said hole, a second servo-motor 27 is provided, acting via a drive belt 28 at the rotatably journaled probe 14. The guides 26 are mounted in an adjustable arrangement with a supporting frame 29, having an edge 30 for positioning said apparatus at a laminate to be inspected.

In an experimentally embodiment of the apparatus according to the invention, use is made of a laser type 007 of Spectra Physics as light source 11. This is a HeNe laser with an output power of 1 mW, a wavelength of 640 nm and a spotsize of 80 $\mu$m. The mirror 12 is provided with a hole of 3 mm, through which the light beam of the laser is directed. In contrast to a semi-transparant mirror, a pierced mirror has the advantage of less internal reflections in the apparatus. The mirror 15 in the probe 14 is a metal mirror, because of being less vulnerable than a mirror of glass or plastic. The doublet lens 17 is a lens from Melles Grit, USA. This lens has a focus of 60 mm and a coating to avoid unwanted reflections.

To perform the angular rotation of the probe 14, the experimental apparatus is equipped with a 12 Volt stepping motor 27 with 400 angular steps, supplied by Astrosyn, USA. The motor is controlled by a stepping motor controller card MSTEP-5, supplied by Metrabyte, and inserted in the processor means 21, shown in FIG. 3. For the vertical (z) translation of the probe 14, the motor 25 is a linear stepping motor supplied by Spectra Physics, USA, having a minimum stepsize of 0.010 mm. However, a stepsize of 0.025 mm will provide also reliable results for average aerospace carbon fibre laminates. This second stepping motor is also controlled by the stepping motor controller card MSTEP-5 of Metrabyte.

For the processor means 21 a personal computer type PS/2 of IBM, having a 20 MB hard disc drive and an 1 MB internal memory. The monitor 25 is an EGA graphics monitor.

The photo-electric detector 18 contains a silicium photodiode integrated with a small electronic amplifier for noise reduction. The electric output signals of said photo-detector are collected and digitized by a DAS 16 F acquisition card of Metrabyte. This card consists of a 16 channel 12 bit A/D converter allowing a sampling rate of 100 kHz. The trigger signals for digitizing the electric output signal of the photo-detector are derived from the MSTEP-5 card which controls the angular rotation, such that with each rotational step a measurement by the detector 18 is executed.

After performing the 400 angular steps of the stepper motor 27, which equals a rotation of 360°, the probe 14 is back at its point of departure. The apparatus is then automatically switched to the acquisition mode, wherein the data measured are read from the DAS 16 card into the memory of the PC 21 by using direct memory access. If applicable, the data corresponding to the first 200 steps will be compared with the data of the second 200 steps. Having stored these data, the probe 14 is translated axially in order to carry out the next 400 measurements. The data of all previous cycles are displayed at the graphics monitor, as shown in FIG. 4. If desired a paper read out may be provided.

Although the invention is illustrated by means of a carbon fiber reinforced plastic laminate, other laminates composed of for example light weight plates, adhered with fiber reinforced synthetic resin, aramide fibers, E-glass fibers etc. are believed to be inspected with the method and apparatus according to the present invention. In a further embodiment, especially suitable for automatic test equipment, drilling means being aligned with the probe means for drilling a hole in the laminate under inspection may be provided.

We claim:
1. A method for non-destructive determination of the stacking order and the fiber orientation of a fiber reinforced composite laminate (1), comprising the steps of:
   illuminating optically successively a series of spots of a cross-sectional surface (6, 7, 8; 10) of a laminate (1) under examination;
   detecting light radiated from respective illuminated spots;
   providing an electrical output signal relative to the amount of light received; and
   forming from said electrical output signal a characterization of the laminate (1) under examination, indic- ative of the stacking order and the fiber orientation thereof.

2. A method according to claim 1, wherein the cross-sectional surface of the composite laminate (1) under examination being the inner surface (10) of a hole (9) in said laminate (1).

3. A method according to claim 1, wherein the cross-sectional surface of the composite laminate (1) under examination being the outside surface of a core sample of said laminate (1).

4. A method according to claim 1, wherein the step of illuminating consists in illuminating successively a series of spots of a first and second sub-surface of said cross-sectional surface of the laminate (1) under examination, said sub-surfaces being mutually reflection symmetric with respect to said illuminated spots, and wherein the step of forming a characterization of the composite laminate (1) under examination includes forming from said first and second sub-surfaces a first and second characterization of said composite laminate (1), respectively, and matching same for generating an indication of the reliability of the results obtained.

5. A method according to claim 4, wherein said cross sectional surface of the composite laminate (1) under examination being the inner surface (10) of a circle cylindrical hole (9) in said laminate (1), the step of illuminating consists in illuminating successively a series of spots in lengthwise (z) and rotational ($\phi$) direction of the inner surface (10) of said hole (9), the first sub-surface being one part of the inner surface (10) of said hole (9) ranging from $\phi=0°$ to $\phi=180°$ and the second sub-surface being another part of the inner surface (10) of said hole (9) ranging from $\phi=180°$ to $\phi=360°$.

6. A method according to claim 4, wherein said cross sectional surface of the composite laminate (1) under examination being the outside surface of a circle cylindrical core sample of said laminate (1), the step of illuminating consists in illuminating successively a series of spots in lengthwise (z) and rotational ($\phi$) direction of the outside surface of said core, the first sub-surface being one part of the outside surface of said core ranging from $\phi=0°$ to $\phi=180°$ and the second sub-surface being another part of the outside surface of said core ranging from $\phi=180°$ to $\phi=360°$.

7. A method according to claim 1, wherein the step of forming a characterization of the composite laminate (1) under examination consists in generating a patch pattern, each patch of which corresponds to a number of adjacently spaced illuminated spots from which the amount of light received is within a given range.

8. A method according to claim 7, wherein the patches are generated such, that their dimensions correspond to the number of adjacently spaced illuminated spots from which the amount of light received is within a given range.

9. A method according to claim 7, wherein the patches are generated in colours, each colour corresponds to the amount of light received within a given range.

10. A method according to claim 1, wherein the step of forming a characterization of the composite laminate (1) under examination consists in forming an electrical representation of said composite laminate (1), comparing same with a given similar known representation of said composite laminate (1), and generating a diagnostic message as a result of said comparison.

11. An apparatus for non-destructive determination of the stacking order and the fiber orientation of a fiber reinforced composite laminate (1), comprising:
light source means (11), for illuminating optically a series of spots of a cross-sectional surface (6,7,8;10) of a composite laminate (1) under examination;
detector means (18), for generating an electrical output signal relative to the amount of light received from an illuminated spot;
probe means (14), optically coupled with said light source means (11) and detector means (18), for providing a light beam to be directed to said cross-sectional surface (6,7,8;10);
drive means (24,25;26,27), for moving relative to each other said probe means (14) and said cross-sectional surface (6,7,8;10) of the composite laminate (1) under examination;
support means (29;23), supporting said light source means (11), detector means (18), probe means (14) and drive means (24,25;26,27), said support means (29) having adjustment means for adjusting said cross-sectional surface (6,7,8;10) of the composite laminate (1) under examination and said probe means (14); and
processor means (21), equipped for controlling said drive means (24,25;26,27) in a programmable manner, and for processing the electrical output signal of said detector means (18) to generate a characterization of the composite laminate (1) under examination indicative of the stacking order and the fiber orientation thereof.

12. An apparatus according to claim 11, wherein the processor means (21) having storage means, for storing the electrical output signal of the detector means (18) in relation to the controlling of the drive means (24,25;26,27), and display means (23) for displaying the generated characterization of the composite laminate (1) under examination.

13. An apparatus according to claim 12, wherein the display means (23) consist in a video monitor, for displaying the generated characterization of the composite laminate (1) under examination as a patch pattern.

14. An apparatus according to claim 11, comprising polarizer means (31) for illuminating the series of spots of said cross-sectional surface (6,7,8;10) of the composite laminate (1) under examination with light of a first polarization, and means (12) for directing to the detector means (18) light of a second polarization received from an illuminated spot.

15. An apparatus according to claim 13, wherein the video monitor is a colour video monitor for displaying the patches in different colours.

* * * * *